US010322058B1

(12) United States Patent
Patch

(10) Patent No.: US 10,322,058 B1
(45) Date of Patent: Jun. 18, 2019

(54) SEXUAL STIMULATION DEVICE

(71) Applicant: Lianna Patch, New Orleans, LA (US)

(72) Inventor: Lianna Patch, New Orleans, LA (US)

( * ) Notice: Subject to any disclaimer, the term of this patent is extended or adjusted under 35 U.S.C. 154(b) by 71 days.

(21) Appl. No.: 15/260,114

(22) Filed: Sep. 8, 2016

Related U.S. Application Data

(60) Provisional application No. 62/215,403, filed on Sep. 8, 2015.

(51) Int. Cl.

| | |
|---|---|
| ***A61F 5/00*** | (2006.01) |
| ***A61H 19/00*** | (2006.01) |
| ***B05B 1/18*** | (2006.01) |
| ***A61H 23/00*** | (2006.01) |
| ***A61H 35/00*** | (2006.01) |
| ***A61H 1/00*** | (2006.01) |
| ***B05B 1/00*** | (2006.01) |

(52) U.S. Cl.
CPC ............. *A61H 19/34* (2013.01); *A61H 1/008* (2013.01); *A61H 19/30* (2013.01); *A61H 23/00* (2013.01); *A61H 35/00* (2013.01); *B05B 1/00* (2013.01); *B05B 1/185* (2013.01); *A61H 2205/087* (2013.01)

(58) Field of Classification Search
CPC ........ A61H 19/00; A61H 19/30; A61H 19/34; A61H 23/00; A61H 37/00; B05B 1/00; B05B 1/14; B05B 1/20
USPC ........................................ 600/38–41; 601/46
See application file for complete search history.

(56) References Cited

U.S. PATENT DOCUMENTS

| | | | | | |
|---|---|---|---|---|---|
| 7,748,649 | B2 * | 7/2010 | Fujii | E03C 1/0408 | 239/436 |
| 7,857,241 | B2 * | 12/2010 | Deng | E03C 1/06 | 239/436 |
| 8,429,769 | B2 * | 4/2013 | Gross | E03C 1/06 | 4/601 |
| 2003/0009116 | A1 * | 1/2003 | Luettgen | A61H 19/34 | 601/46 |
| 2006/0111608 | A1 * | 5/2006 | Kennedy | A61H 19/00 | 600/38 |
| 2011/0266363 | A1 * | 11/2011 | Lee | B05B 1/083 | 239/102.1 |
| 2013/0261385 | A1 * | 10/2013 | Zipper | A61H 19/40 | 600/38 |

* cited by examiner

*Primary Examiner* — John P Lacyk
(74) *Attorney, Agent, or Firm* — Eric L. Sophir; Dentons US LLP

(57) ABSTRACT

Disclosed herein are sexual stimulation devices that attach to a shower hose. The devices include a showerhead body and a shower hose-engaging structure to connect the showerhead body to the shower hose. The showerhead body has a plurality of water ports for directing water flowing from the shower hose and a vibrator to produce vibrations for external sexual stimulation. The vibrator can be battery-powered or water-powered units.

16 Claims, 16 Drawing Sheets

SEXUAL STIMULATION DEVICE

CROSS REFERENCE TO RELATED APPLICATIONS

This application claims the benefit of U.S. Provisional Application No. 62/215,403, filed Sep. 8, 2015.

TECHNICAL FIELD

The present invention generally relates to a sexual stimulation device and more particularly to a sexual stimulation device that includes a vibratory component and attaches to an end of a shower hose.

BACKGROUND

Electronic devices for sexual pleasure and luxury showerheads are both well-documented in the art; however, the market sorely lacks a high-quality, unisex toy option that combines the two. Shower sex has long been romanticized and fantasized about by both men and women, who desire a pleasure offered by the combination of a hot shower with sexual stimulation. In the same vein, it is understood in the art that a handheld showerhead can function as a masturbation device; the handheld showerhead has even been recommended as a "DIY sex toy" by sexual education authority Scarleteen.

However, several health and safety issues arise when repurposing a standard handheld showerhead as a sex toy. The showerhead may contain sharp edges or protrusions that can harm the user. It may also harbor dangerous bacteria, which can easily proliferate on a toy's warm, wet, hard-to-clean areas. It also does not offer a vibratory option so the user has to rely on water pressure and jets for stimulation.

There are other devices that can attach directly to a shower hose designed for a handheld shower, but those devices are penetrative, requiring insertion into a vagina or anus for use. This quality renders them overly exclusive. The market still lacks a non-penetrative, shower-based stimulation option. The market has a rapidly growing desire for devices that combine the enjoyment of a hot shower with the enjoyment of sex or sexual play.

SUMMARY

Disclosed herein are apparatuses and systems that address the shortcomings of the art, and may provide any number of additional advantages, such as having smooth contours, being easy to clean, and made of high-quality materials that do not easily foster the growth of bacteria. In certain embodiments, the device is a non-penetrative, vibrating showerhead that is removably coupled to a handheld shower hose to receive water flow therefrom. Certain embodiments of this physically stimulating showerhead function as high-quality electronic sex toys with control mechanisms and power sources, such as rechargeable batteries. The electronic components can be covered in body-safe silicone or a similar material, making the device waterproof and safe for use while bathing or showering. The device is designed to stimulate external genitalia, including but not limited to the clitoris, while spraying or pulsing water jets. As the device can be charged using a rechargeable battery, it is more convenient and eco-friendly to use than conventional stimulatory devices that use disposable batteries.

Convenience, comfort, privacy, and ease of cleaning are all considerations for sex toys. The devices described herein can remain in the shower when not in use. Their discreet design and easy-to-attach shower hose connector allows them to blend in with the bathroom environment, so that owners wishing to maintain their privacy need not remove it with each use. It features minimal folds or crevices where bacteria could potentially breed, and can easily be cleaned with soap and water.

Unlike conventional devices, this device can be used for the sexual enjoyment of all bodies: male, female, and any one identifying as "other". In addition, it is designed to be easily used in between two bodies, if desired. The shape of the device can conform to various bodily curves, and can stimulate two bodies simultaneously when placed in between bodies and held there.

Disclosed herein are sexual stimulation devices that include a showerhead body and a shower hose-engaging structure to connect the showerhead body to the shower hose. The showerhead body contains a plurality of water ports for directing water flowing from the shower hose and a battery-powered vibrator to produce vibrations for sexual stimulation. The showerhead body can include a regulator to control intensity of the vibrations from the vibrator. The vibrator can be removably or irremovably engaged with the showerhead body. The vibrator can be housed inside the showerhead body. The plurality of water ports can be located on an anterior surface of the showerhead body. The plurality of water ports can be located on an anterior surface and a posterior surface of the showerhead body. A plurality of controls for the regulator can be located on a posterior surface of the showerhead body. The control for the regulator can be located between the shower hose-engaging structure and the showerhead body. The exterior of the showerhead body can be a single piece of molded plastic. The exterior of the showerhead body can be covered by a silicone sheath. The sexual stimulation device can include a handle attached to a posterior surface of the showerhead body.

In another embodiment, the showerhead body contains a plurality of water ports for directing water flowing from the shower hose and a water-powered vibrator to produce vibrations for sexual stimulation. The showerhead body can include a flow regulator to control intensity of the vibrations from the vibrator. The control for the regulator can be located between the shower hose-engaging structure and the showerhead body. The plurality of water ports can be located on an anterior surface of the showerhead body. The exterior of the showerhead body can be a single piece of molded plastic. The exterior of the showerhead body can be covered by a silicone sheath. The anterior surface of the showerhead body can be a textured surface.

In another embodiment, the showerhead body has a two-pronged structure. The plurality of water ports can be located at the base of the two-pronged structure or distributed on the surface of the two prongs.

It is to be understood that both the foregoing general description and the following detailed description are exemplary and explanatory and are intended to provide further explanation of the invention as claimed. Numerous other aspects, features and benefits of the present disclosure may be made apparent from the following detailed description taken together with the drawing figures.

BRIEF DESCRIPTION OF THE DRAWINGS

The accompanying drawings constitute a part of this specification, illustrate an embodiment of the invention, and together with the specification, explain the invention. The present disclosure can be better understood by referring to the following figures. The components in the figures are not necessarily to scale, emphasis instead being placed upon illustrating the principles of the disclosure.

DETAILED DESCRIPTION

Figure 1:
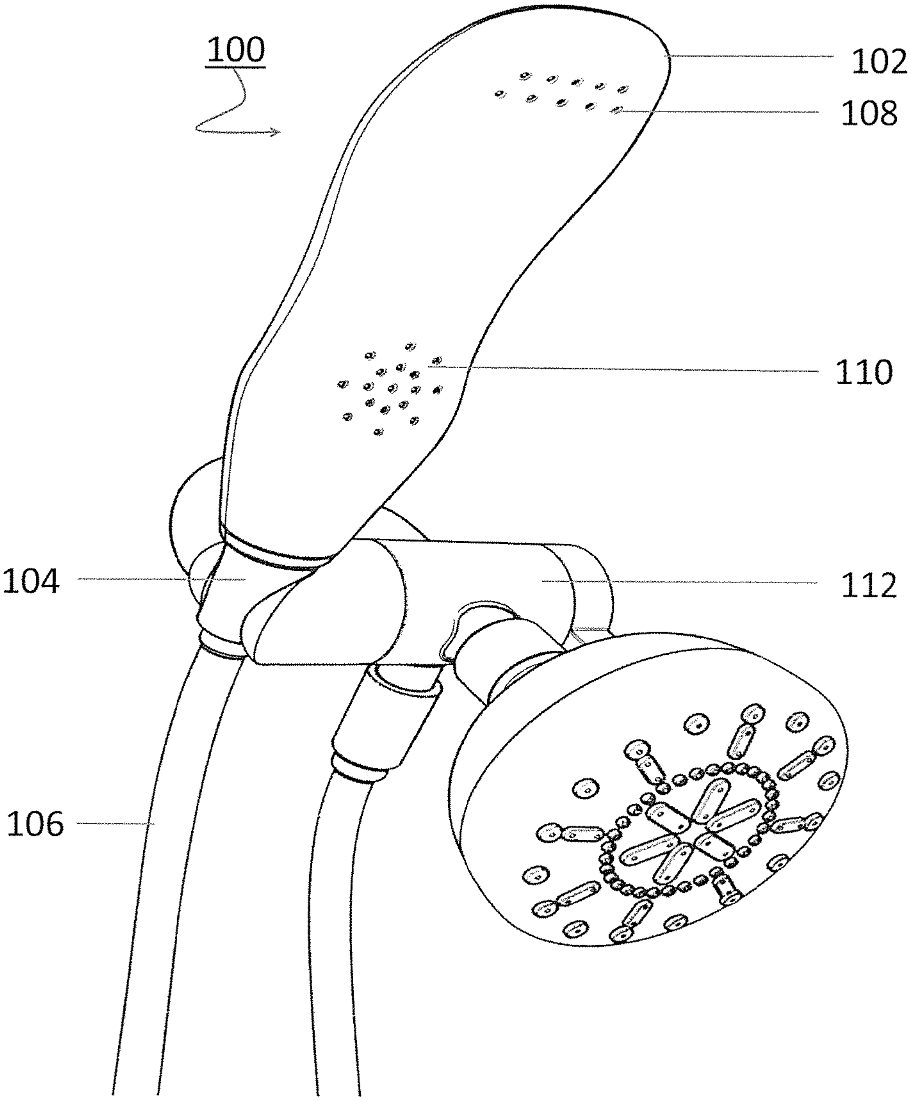
FIG. 1 is a diagrammatic representation of a sexual stimulation device when coupled to an end of a shower hose, according to an exemplary embodiment.

Reference will now be made to the exemplary embodiments illustrated in the drawings, and specific language will be used here to describe the same. It will nevertheless be understood that no limitation of the scope of the invention is thereby intended. Alterations and further modifications of the inventive features illustrated here, and additional applications of the principles of the inventions as illustrated here, which would occur to one skilled in the relevant art and having possession of this disclosure, are to be considered within the scope of the invention.

FIG. 1 is a diagrammatic representation of an external sexual stimulation device when coupled to an end of a shower hose, according to an exemplary embodiment. The sexual stimulation device 100 has a showerhead body 102 and a mechanism 104 for attaching the showerhead body to a handheld showerhead hose 106. The device can be attached to a standard, handheld shower hose connection or may use a "Quick Connect" snap mechanism or a "push-to-connect" mechanism for increased ease of removal and installation.

The showerhead body 102 of the sexual stimulation device 100 also has several water outlet zones 108 and 110. The water stream delivered by the hose 106 to the showerhead body 102 is expelled through water outlet zones 108 and 110. The water outlet zones 108 and 110 have several ports and can be controlled to produce water jets of varying flow rates and intensities, such as a fine mist, a strong spray, or a pulsating stream. The ports can be arranged in rows as in outlet zone 108, or in a radial manner as in outlet zone 110, or in any regular or random manner. For example, the ports can be arranged in a concentric circular arrangement. The ports can be arranged in horizontal rows or in vertical rows of varying lengths. The ports can be arranged as a single row of jets positioned around the perimeter of the anterior surface or can be arranged to occupy substantial surface of the anterior side of the device. The anterior surface, as used herein, refers to the surface of the sexual stimulation device closest to or facing the user during operation of the sexual stimulation device. The posterior surface, as used herein, refers to the surface of the sexual stimulation device that is away from the user's body. In certain embodiments, the posterior surface of the sexual stimulation device can be facing or in contact with a second user's body.

In an embodiment of the device, only the anterior side possesses water outlet zones, as shown in FIG. 1. In another embodiment, water outlet zones are present on the anterior and posterior sides of the showerhead body of the sexual stimulation device. In another embodiment, water outlet zones are present on edges of the showerhead body of the sexual stimulation device. These devices facilitate water-based stimulation for multiple users when the device is used in such manner.

The device 100 is depicted as it would be placed in a bathtub or shower stall, alongside a non-handheld, traditional showerhead 112. When the user turns on the shower, water will automatically be directed to the device. The user can leave the device on a hook in order to use it as a regular showerhead or choose to activate the vibration modes.

Figure 2:
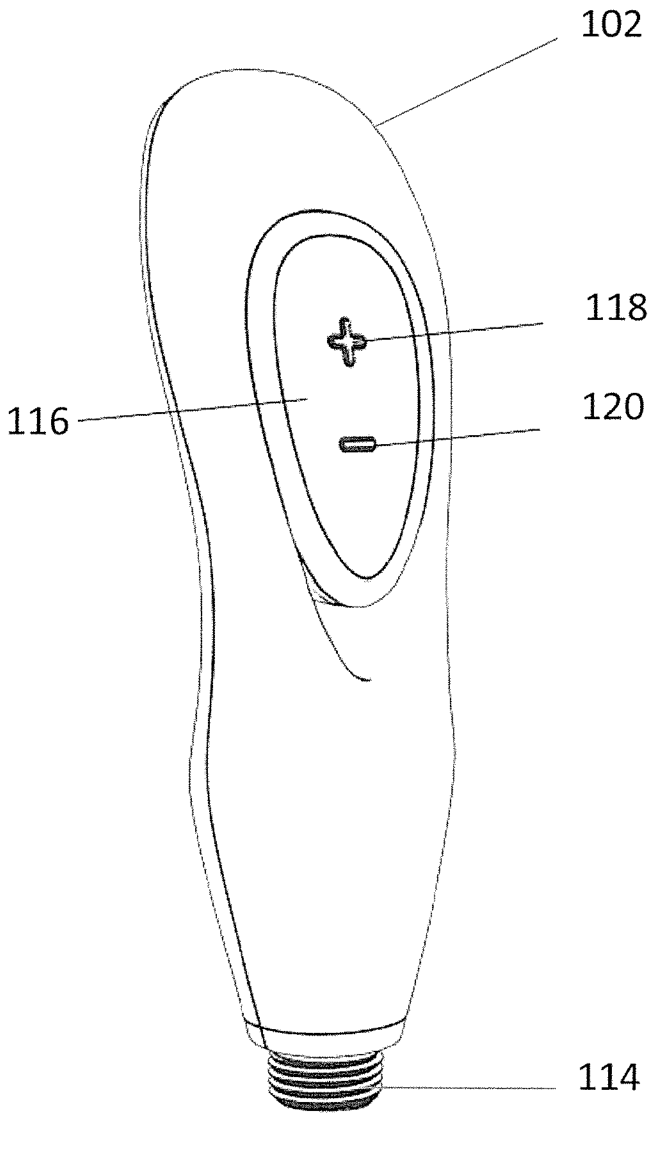
FIG. 2 is a diagrammatic representation of the posterior view of the sexual stimulation device, according to an exemplary embodiment.

FIG. 2 is a diagrammatic representation of the posterior view of the sexual stimulation device 100, according to an exemplary embodiment. The showerhead body 102 of the sexual stimulation device has a curved, paddle-like shape, which can be applied to various bodily curves and surfaces, and has a screw-in mechanism 114 to couple the device to a shower hose. Also shown here is the vibratory component or the vibrator 116 that has haptic controls 118 and 120 for increasing and decreasing the vibratory speed, respectively. Upon activating the vibrator, the showerhead vibrates. Use of the regulatory means enables the showerhead to produce a range of vibrations from mild to intense, according to the user's preference. In another embodiment, the device may feature a dial or other selective mechanism to control the vibration.

In an embodiment, the showerhead body 102 of sexual stimulation device 100 is designed as a thin structure such that it can fit between two bodies if the users decide to employ the device in this fashion. In another embodiment of the device, the showerhead body may have a thicker, rounded posterior curve that comfortably conforms to the user's palm. In another embodiment of the device, the showerhead body may be shaped such that both the anterior and posterior sides possess a gentle concave shape, conforming to curved body areas. In another embodiment of the device, the anterior surface of the showerhead body of the sexual stimulation devices may present a cup-like shape in order to provide suction. In another embodiment, the showerhead body may include a handle, made of body-safe silicone or a similar material, on the posterior side to improve the user's grip on the device. In certain embodiments, the dimensions of the device 100, such as its length, width, height, and shape can be altered to create variability in water pressure.

In certain embodiments, the anterior side of the showerhead body 102 of sexual stimulation device 100 possesses a textured surface. In another embodiment, both the anterior and posterior sides possess a textured surface. The texture can be achieved via raised nubs, bumps, or protuberances of different shapes and sizes. The textured surface can be arranged in between the water outlet zones 107 and 108, or in any regular or random manner. For example, the protuberances can be arranged in a concentric circular arrangement, or in horizontal rows or in vertical rows of varying lengths. The protuberances can be designed to convey the vibrations from the vibrator.

The showerhead body 102 of the sexual stimulation device 100 can be covered in an FDA-approved, nonporous material such as silicone. It is desirable to use a material that will not degrade with exposure to water, and may be cleaned with gentle soap and water. In certain embodiments of the device, the body-safe "skin" covering the showerhead body 102 of sexual stimulation device 100 may be removable for ease of cleaning.

Figure 3:
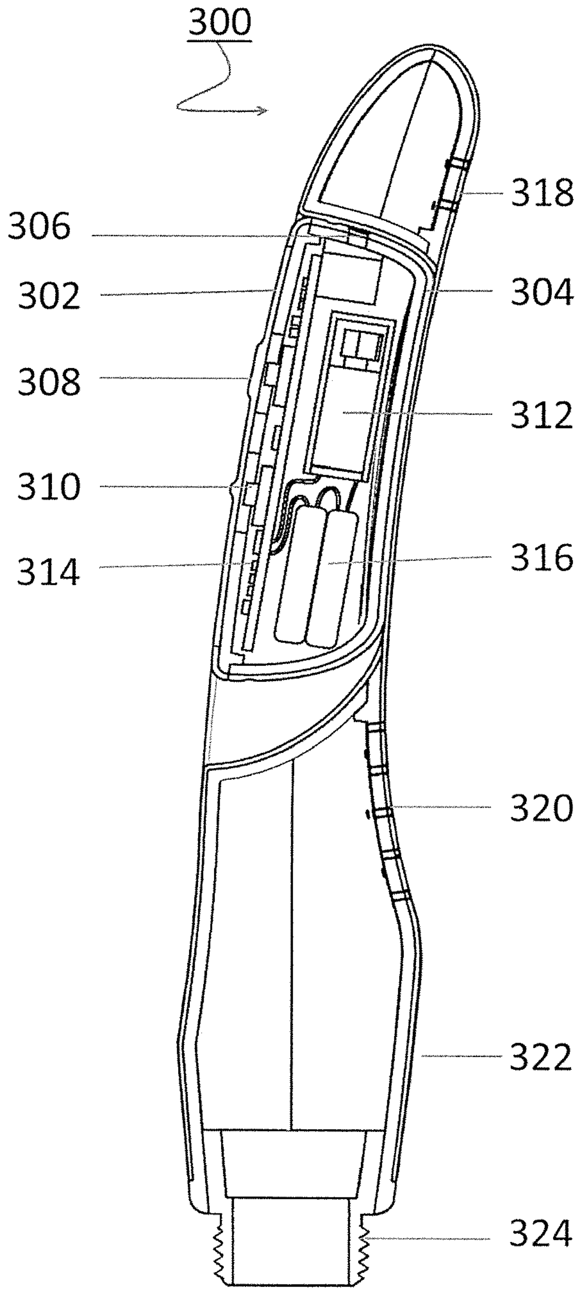
FIG. 3 is a diagrammatic representation of a cross-section of the sexual stimulation device, according to an exemplary embodiment.

FIG. 3 is a diagrammatic representation of a cross-section of the sexual stimulation device 300 with a removable vibrator 302 placed within the showerhead body 304, according to an exemplary embodiment. The vibrator 302 includes a waterproof charging port 306, tactile button switches 308 and 310, encapsulated vibrating motor 312, printed circuit board 314, rechargeable battery pack 316. In this embodiment, the vibrator 302 has an electromechanical motor with an output shaft that supports a counterweight or eccentric mass. The motor can be a DC micromotor, brushless motor, adjustable resonating motor, servomotor, stepper motor, or any other suitable type of motor of any other size. The showerhead body 304 of the sexual stimulation device 300 also has upper water jet ports 318 and lower water jet ports 320 that are configured to be above and below the vibrator. The showerhead body 304, including the vibrator 302 is fitted by an overmolded body-safe silicone sheath 322. The sexual stimulation device 300 is depicted with a ½-inch standard NPT threaded mechanism 324 for attaching the showerhead body to a handheld showerhead hose.

Figure 4:
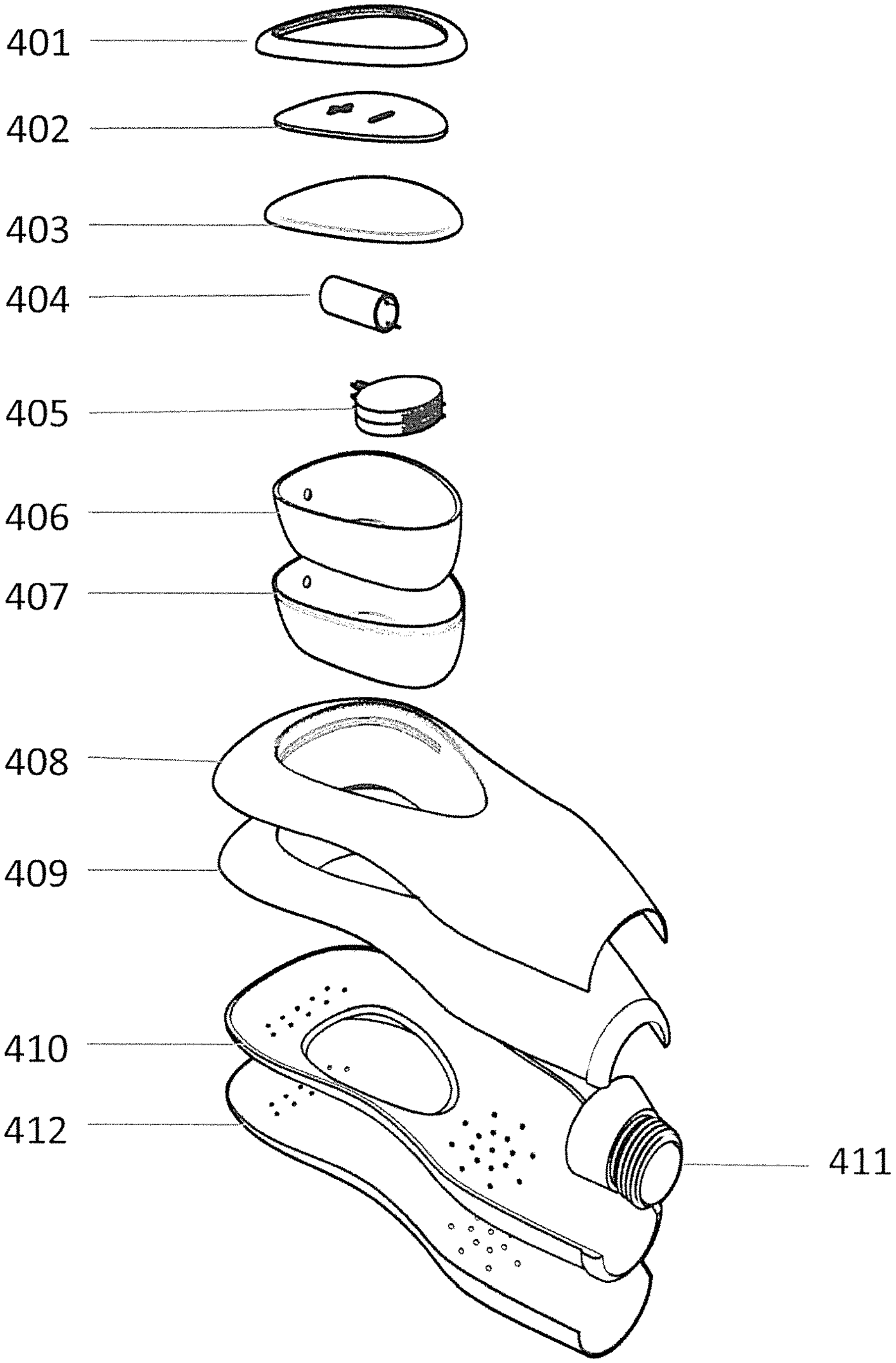
FIG. 4 is a diagrammatic representation of an exploded view of the components of a sexual stimulation device, according to an exemplary embodiment.

FIG. 4 is a diagrammatic representation of an exploded view of the components of a sexual stimulation device, according to an exemplary embodiment. The components of the vibrator include an external ring 401, tactile control plate 402, regulator 403 connecting the control plate 402 to the encapsulated vibrating motor 404, rechargeable battery pack 405, bottom case 406, and an body-safe silicone vibrator sheath 407. The vibrator engages with the upper portion 408 of a body-safe silicone showerhead body sheath and the posterior part 409 of the showerhead body through a slot or groove. The silicone showerhead body sheath snugly fits the posterior part 409 and anterior part 410 of the showerhead body via the upper portion 408 and the lower portion 411 of a body-safe silicone showerhead body sheath, while leaving the threaded mechanism 412 open for engagement with the shower hose.

Figure 5:
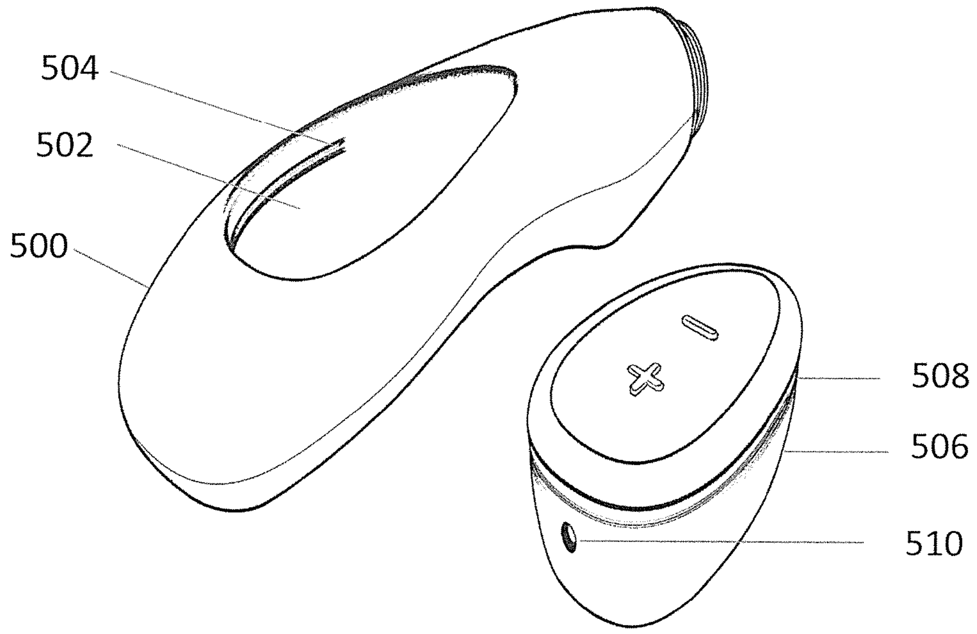
FIG. 5 is a diagrammatic representation of the sexual stimulation device with the vibrator removed from the showerhead body, according to an exemplary embodiment.

FIG. 5 is a diagrammatic representation of the sexual stimulation device with the vibrator removed from the showerhead body, according to an exemplary embodiment. The showerhead body 500 of the sexual stimulation device has an inner opening 502 with a slot 504. The vibrator 506 fits into the opening 502 on the showerhead body 500 using an insert 508 that runs on the upper periphery of the vibrator 506 and engages with the slot 504. The vibrator 506 can securely engage with the opening 502 in a variety of ways, including but not limited to a snap-groove or a snap-clip engagement. The vibrator 506 also has a charging port 510 that connects the vibrator to a power source to charge the battery. In an embodiment of the device, the vibrator's silicone sheath may include a small flap or plug that further protects the charging port while the device is in use.

Figure 6:
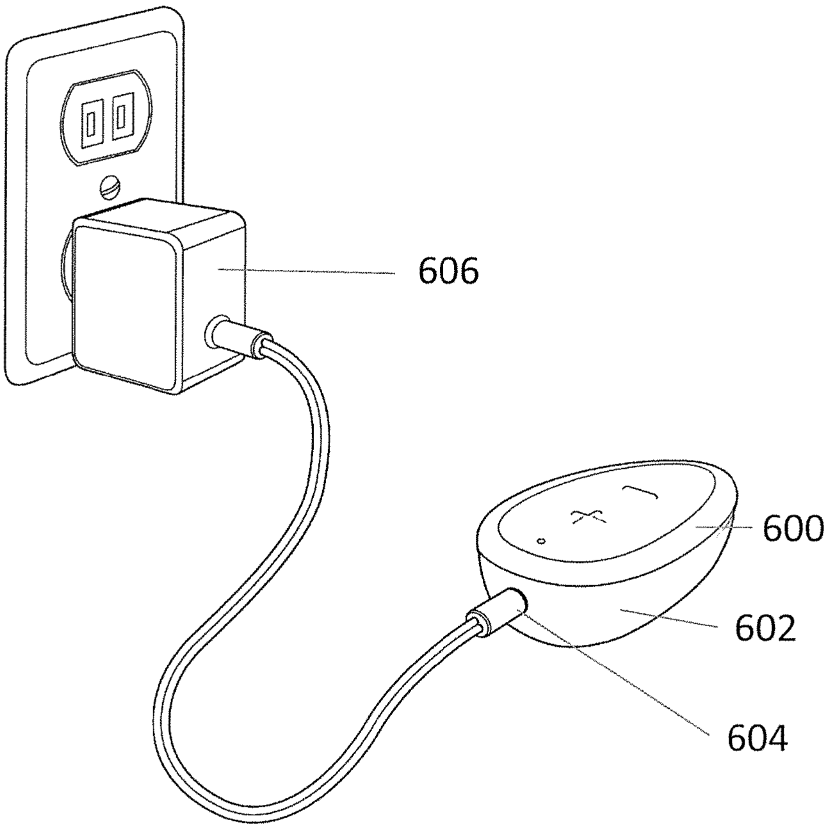
FIG. 6 is a diagrammatic representation of the vibrator being charged using a specific charger, according to an exemplary embodiment.

FIG. 6 is a diagrammatic representation of the vibrator being charged using a specific charger, according to an exemplary embodiment. The vibrator 600 has a female charging port 602 that engages with a male electrical charging jack 604 to charge the battery. The male electrical charging jack 604 connects the vibrator directly to an electrical wall outlet using a plug 606. In an embodiment, the vibrator can be powered by a voltage supply or battery that may be charged via a USB female charging port and male USB cable.

Figure 7:
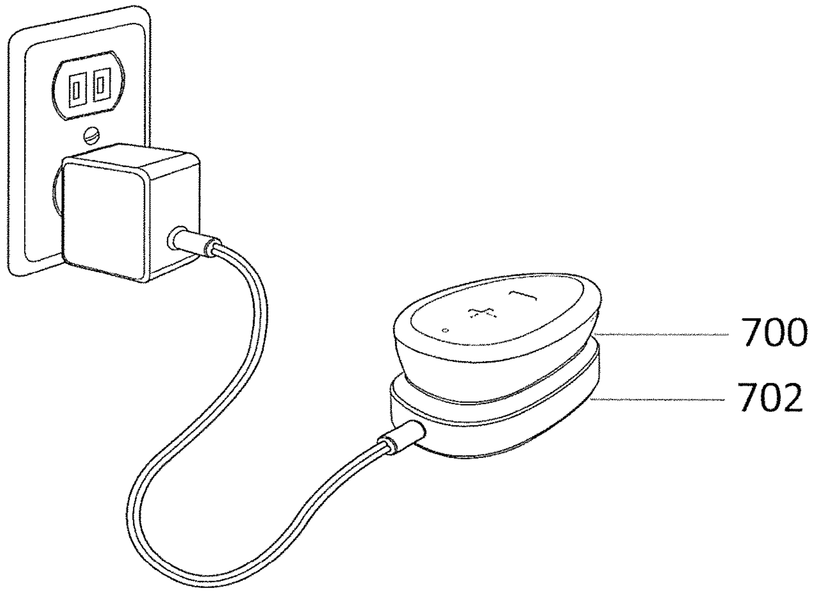
FIG. 7 is a diagrammatic representation of the vibrator being charged using an inductive charging station, according to an exemplary embodiment.

FIG. 7 is a diagrammatic representation of the vibrator being charged using a wireless charging station, according to an exemplary embodiment. The vibrator 700 is placed on a wireless charging station, such as the inductive charger 702 to charge the battery. Vibrators in this embodiment are configured to be Qi compatible.

Figure 8:
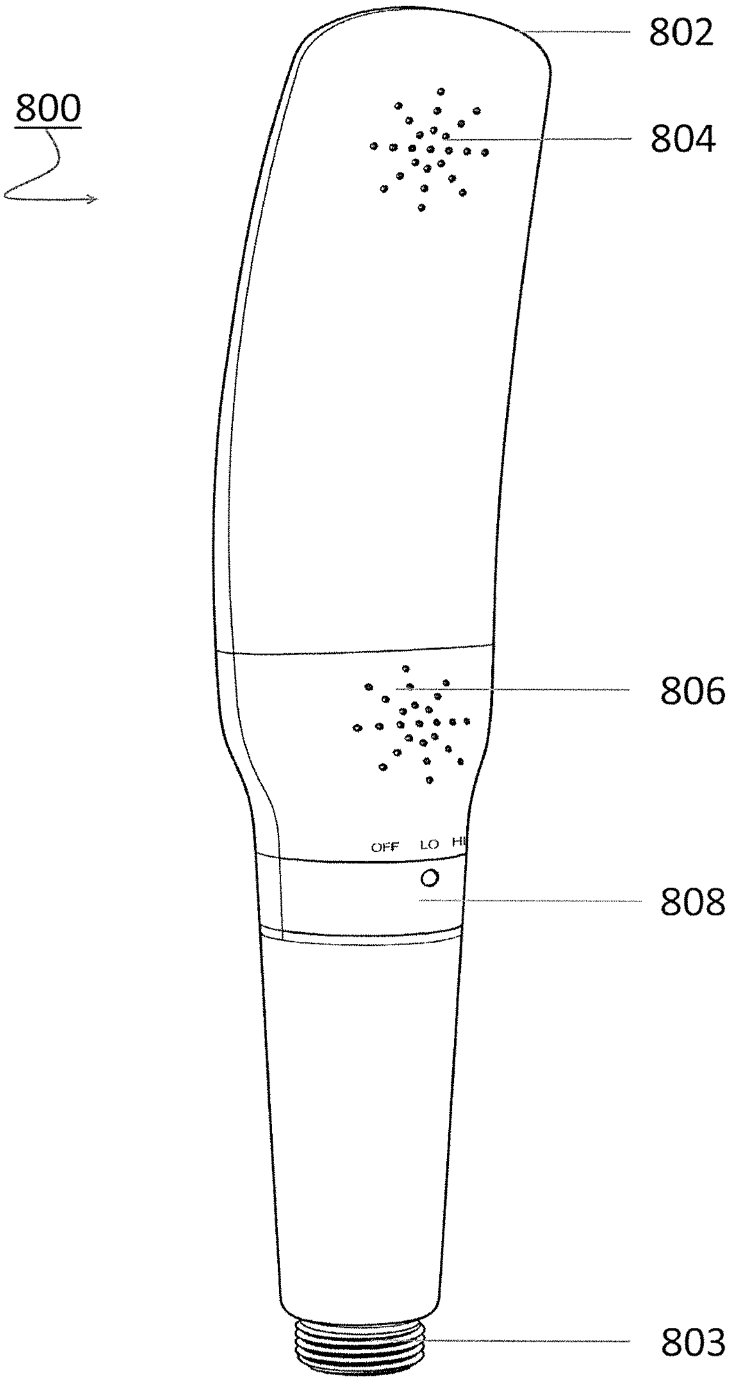
FIG. 8 is a diagrammatic representation of a sexual stimulation device with a water-powered vibrator, according to an exemplary embodiment.

FIG. 8 is a diagrammatic representation of a sexual stimulation device with an in-built water-powered vibrator, according to an exemplary embodiment. The sexual stimulation device 800 has a showerhead body 802 and a mechanism 803 for attaching the showerhead body to a handheld showerhead hose 106. The device can be attached to a standard, handheld shower hose connection or may use a "Quick Connect" snap mechanism or a "push-to-connect" mechanism for increased ease of removal and installation.

The showerhead body 802 of the sexual stimulation device 100 has several water outlet zones 804 and 806. The water outlet zones 804 and 806 have several ports and can be controlled to produce water jets of varying flow rates and intensities, such as a fine mist, a strong spray, or a pulsating stream. The ports can be arranged in a radial manner as in outlet zones 804 and 806, or as rows or in any regular or random manner. For example, the ports can be arranged in a concentric circular arrangement. The ports can be arranged in horizontal rows or in vertical rows of varying lengths. The ports can be arranged as a single row of jets positioned around the perimeter of the anterior surface or can be arranged to occupy substantial surface of the anterior side of the device. In an embodiment of the device, only the anterior side possesses water outlet zones, as shown in FIG. 8. In another embodiment, water outlet zones are present on the anterior and posterior sides of the showerhead body of the sexual stimulation device. In another embodiment, water outlet zones are present on edges of the showerhead body of the sexual stimulation device. These devices facilitate water-based stimulation for multiple users when the device is used in such manner. This embodiment contains an inbuilt vibrator (not shown here) that is regulated via controller 808. This controller 808 can have settings such as "Off, Low, and High," or "Off, 1, 2, and 3" to increase the intensity of the vibrations.

Figure 9:
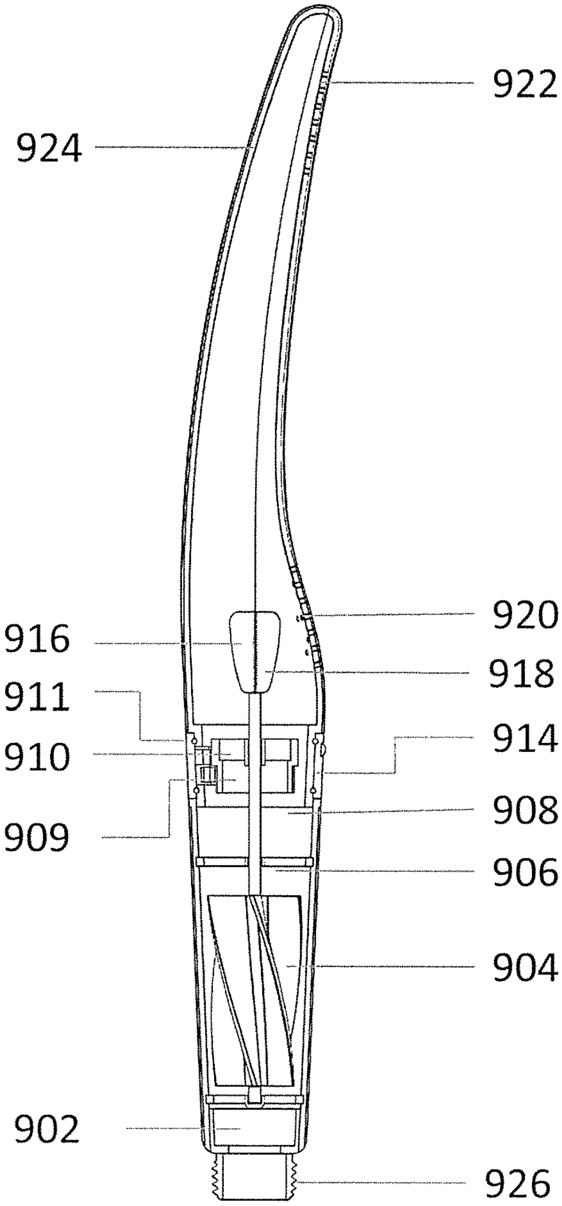
FIG. 9 is a diagrammatic representation of a cross-section of the sexual stimulation device with a water-powered vibrator, according to an exemplary embodiment.

FIG. 9 is a diagrammatic representation of a cross-section of the sexual stimulation device with a water-powered vibrator, according to an exemplary embodiment. The components of the vibrator include drive shaft bracket 902 connected to a water-driven propeller 904 and a drive shaft 906. The vibrator also includes a brake system 908 that includes "Off" vibration setting mechanism 909 and "Low" vibration setting mechanism 910. There is a waterproof O-ring gasketing 912. The external surface of this system has a molded indicator 914 that helps regulate the vibrator intensity through a twist or an adjustable ring mechanism. The shaft 906 has a vibrating mechanism or a revolved form composed of two halves—a weighted half 916 and an unweighted half 918. The weighted section 916 functions as an eccentric rotating mass. As the shaft rotates, the centripetal force of the weighted section is asymmetric, resulting in a net centrifugal force that slightly displaces the shaft. This displacement is perceived as vibration. The showerhead body of the sexual stimulation device has lower water jet ports 920 and upper water jet ports 922 that are configured to work independently or in conjunction with the vibrator. A silicone showerhead body sheath 924 snugly fits the injection-molded plastic showerhead body of the device, while leaving the threaded mechanism 926 open for engagement with the shower hose.

Figure 10:
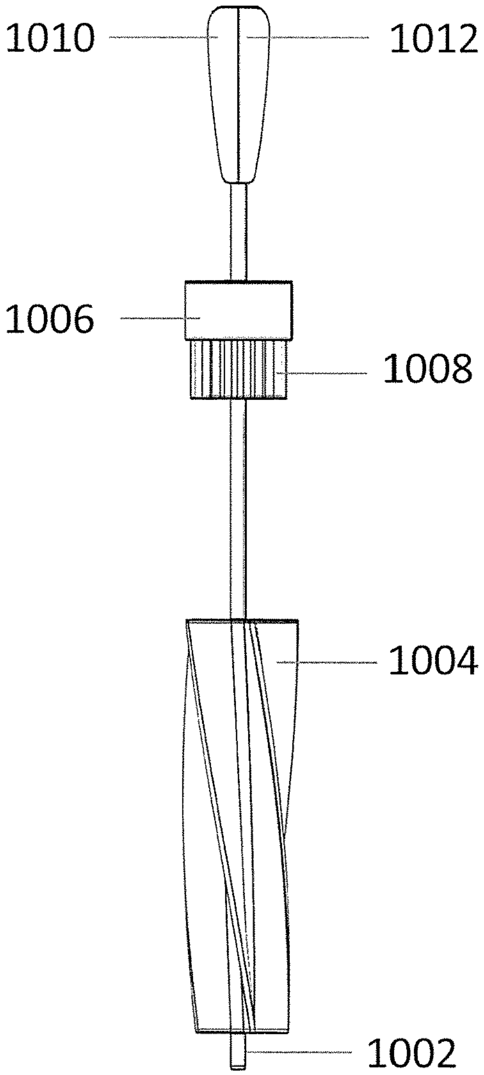
FIG. 10 is a diagrammatic representation of certain components of the sexual stimulation device with a water-powered vibrator, according to an exemplary embodiment.

FIG. 10 is a diagrammatic representation of water propeller components of the sexual stimulation device with a water-powered vibrator, according to an exemplary embodiment. The drive shaft 1002 is connected to a water-driven propeller 1004. The brake system on the shaft includes a brake mechanism 1006 and a toothed rotational stop mechanism 1008, along with a vibrating mechanism or a revolved form composed of two halves—a weighted half 1010 and an unweighted half 1018. The cross section of the two halves combined is a circle and this form is uninhibited as water rushes past it.

Figure 11A:
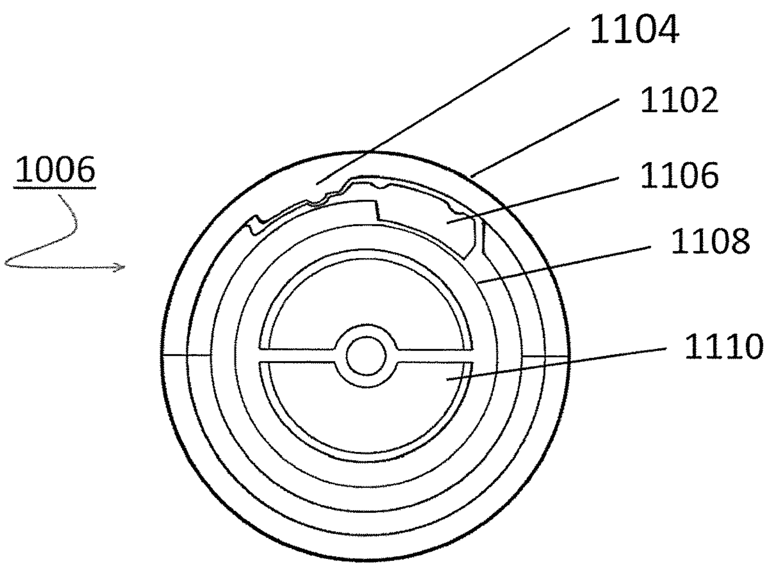
FIGS. 11A and B are diagrammatic representations of the cross-sections of the "OFF" and "LOW" positions of the sexual stimulation device with a water-powered vibrator, according to an exemplary embodiment.

FIG. 11A is a diagrammatic representation of the cross-section of the brake mechanism 1006 of the sexual stimulation device with a water-powered vibrator, according to an exemplary embodiment. As the outer ring 1102 of the brake mechanism 1006 rotates to the "Low" position on the indicator, a ramped surface 1104 forces another component 1106 to flex downward, acting as a slowing mechanism against the surface 1108 affixed to the drive shaft 1002.

Figure 11B:
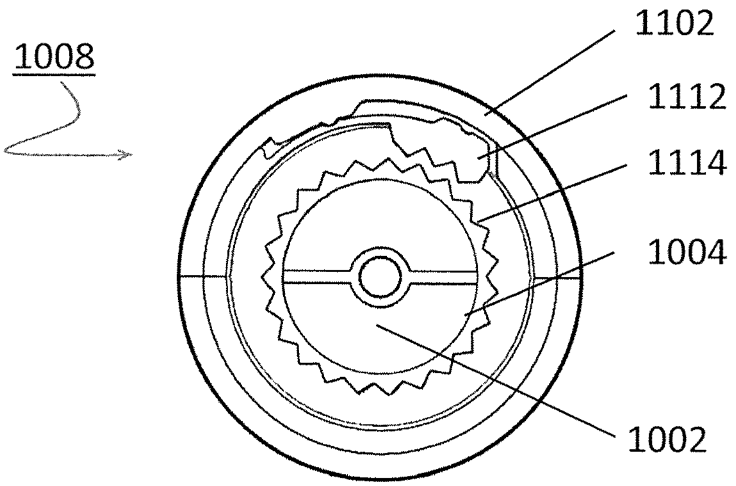

FIG. 11B is a diagrammatic representation of the cross-section of the toothed rotational stop mechanism 1008 of the sexual stimulation device with a water-powered vibrator, according to an exemplary embodiment. When the outer ring 1102 of the brake mechanism 1006 rotates to its farthest position ("stop" or "off"), its toothed surface 1112 engages with the teeth of the cog element 1114 of the propeller 1004, and thus brings the vibratory action, to a full stop.

Figure 12A:
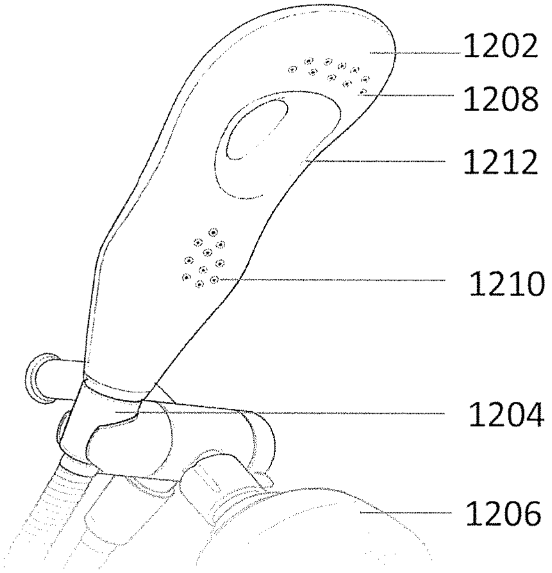
FIGS. 12A-D are diagrammatic representations of the vibrator used independently of the sexual stimulation device, according to an exemplary embodiment.

FIG. 12A is a diagrammatic representation of the sexual stimulation device with the vibrator removed from the showerhead body, according to an exemplary embodiment. The sexual stimulation device has a showerhead body 1202 and a mechanism 1204 for attaching the showerhead body to a handheld showerhead hose 1206. The showerhead body 1202 has several water outlet zones 108 and 110. The water stream delivered by the hose 106 to the showerhead body 102 is expelled through water outlet zones 1208 and 1210. The water outlet zones 1208 and 1210 have several ports and can be controlled to produce water jets of varying flow rates and intensities, such as a fine mist, a strong spray, or a pulsating stream. The ports can be arranged in rows as in outlet zone 1208, or in a random manner as in outlet zone 1210. The showerhead body 1202 of the sexual stimulation device has an opening 1212. The vibrator 1214 fits into the opening 1212 on the showerhead body 1202 securely in a variety of ways, including but not limited to a snap-groove or a snap-clip engagement.

Figure 12B:
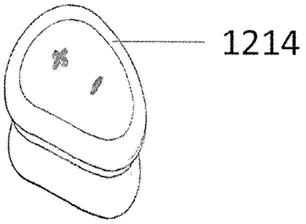

FIG. 12B is a diagrammatic representation of the vibrator 1214 removed from the showerhead body 1202 of the sexual stimulation device, according to an exemplary embodiment.

Figure 12C:
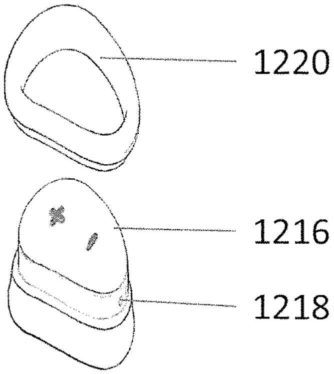

FIG. 12C is a diagrammatic representation of an exploded view of the components of the vibrator 1214 removed from the showerhead body 1202 of the sexual stimulation device, according to an exemplary embodiment. The components of the vibrator include a tactile controls plate 1216, charging port 1218, and a removable ring 1220 that covers the charging port.

Figure 12D:
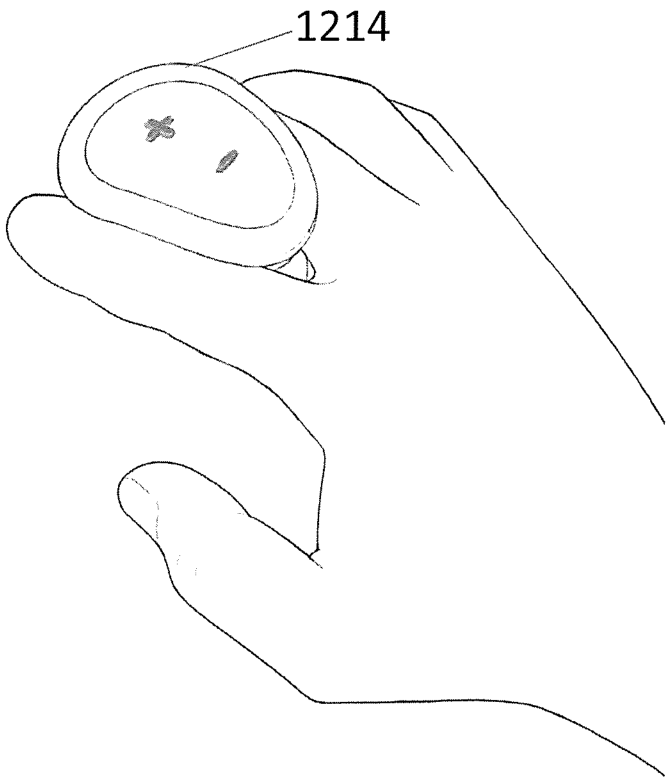

FIG. 12D is a diagrammatic representation of the vibrator used independently of the sexual stimulation device, according to an exemplary embodiment. The vibrator 1214 is designed with curved surfaces such that it can be held comfortably between two fingers of the user's hand.

Figure 13A:
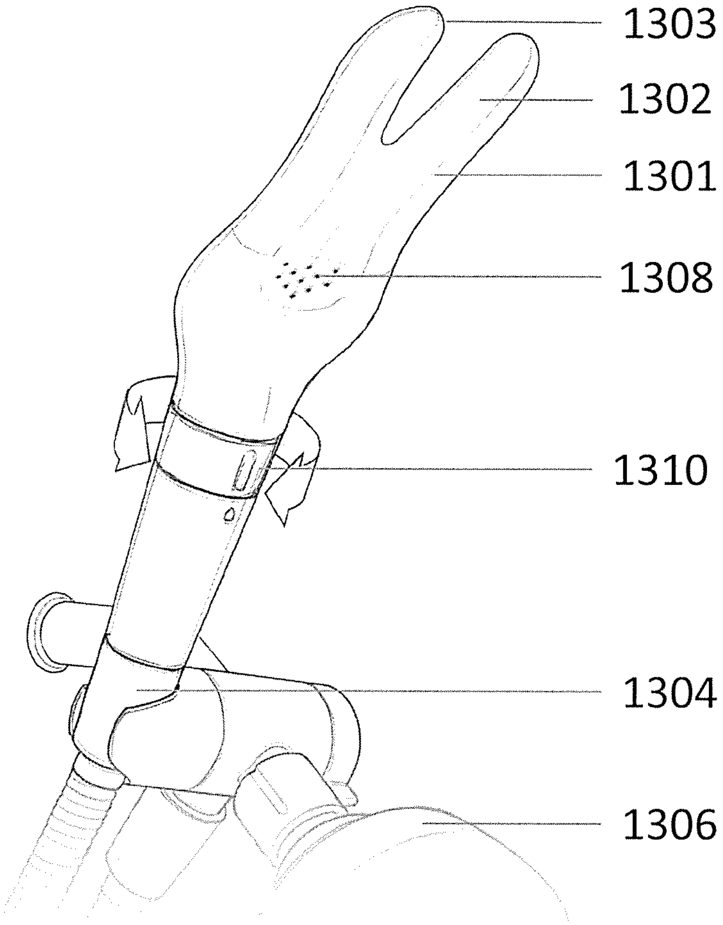
FIGS. 13A and B are diagrammatic representations of certain components of the sexual stimulation device with a water-powered vibrator, according to an exemplary embodiment.

FIG. 13A is a diagrammatic representation of a sexual stimulation device with a split showerhead body structure, according to an exemplary embodiment. The sexual stimulation device has a showerhead body 1301 with a split structure with two prongs 1302 and 1303, and a mechanism 1304 for attaching the showerhead body to a handheld showerhead hose 1306. The showerhead body 1301 has a water outlet zone 1308 with all the water jet ports near the base of the showerhead. In another embodiment, the water jets extend along the sides of the two prongs. An adjustable or twist wheel 1310 is used to control the flow of water exiting the water jet ports.

Figure 13B:
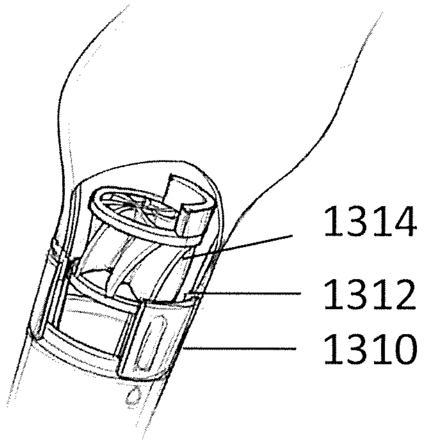

FIG. 13B is a diagrammatic representation of the water propeller system of a sexual stimulation device with a split showerhead body structure, according to an exemplary embodiment. In this embodiment where an adjustable wheel 1310 is used to control water flow, the showerhead may be able to be configured to produce several sprays, whereby a user can select a desired spray setting. Between the housing and the nozzle plate, a guide plate (not shown) has passages and a wheel 1312 with radially extending and annularly arranged vanes 1314, apertured regions, and blocking regions. The water is directed by the passages to the wheel to set it in rotation. The apertured regions and the blocking regions of the wheel rapidly cover and uncover the underlying openings of the nozzle plate as the wheel rotates so that a pulsating spray is produced. Rotating the nozzle shutter relative to the nozzle plate can also change the water spray. In one embodiment of the device, wherein more than one prong of the device includes water jets, the device can have a turnable on/off wheel, cap, plug, or other cover to allow the user(s) to shut off water flow to that prong of the device. The showerhead body with the two prongs can be configured to include the water-powered vibrator mechanism described in FIGS. 9, 10, 11A and 11B.

Figure 14A:
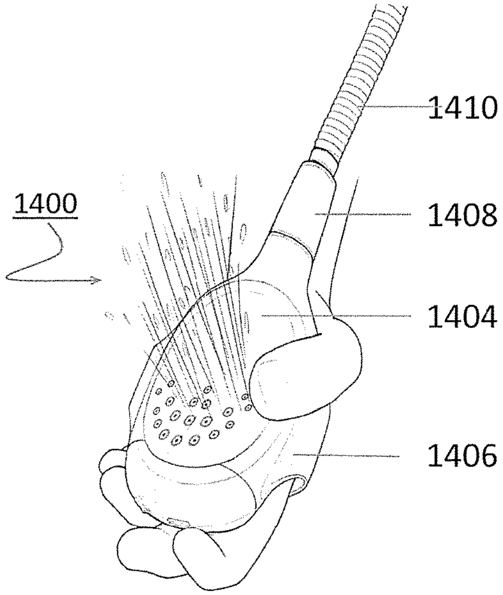
FIGS. 14A and B are diagrammatic representations of certain components of the sexual stimulation device with a water-powered vibrator, according to an exemplary embodiment.
Figure 14B:
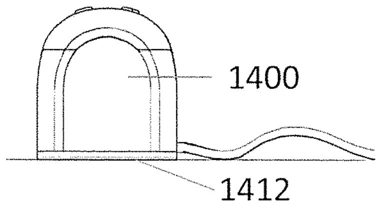

FIG. 14A is a diagrammatic representation of a sexual stimulation device with a hand-held handle, according to an exemplary embodiment. This device 1400 includes a showerhead body 1402 with a removable electronic vibration unit 1404 and a hand strap 1406 on the posterior side for improved grip. The hand strap 1406 is made of body-safe silicone or a similar material and is designed to provide excellent wet or dry grip. The hand strap 1406 can include high vibration dampening materials, thus providing greater comfort during use. The sexual stimulation device 1400 also includes a mechanism 1408 for attaching the showerhead body to a handheld showerhead hose 1410. FIG. 14B is a diagrammatic representation of the sexual stimulation device 1400 being charged using a wireless charging station, according to an exemplary embodiment. The device 1400 is placed on a wireless charging station, such as the inductive charger 1412 to charge an internal battery. Devices in this embodiment can be configured to be Qi compatible.

The preceding description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein.

The invention claimed is:

1. A sexual stimulation device, the device comprising:

a shower hose-engaging structure to connect a showerhead body to a shower hose, where the showerhead body has a first side and a second opposing side, each of the first side and the second side being substantially flat and curving toward an edge around the perimeter that adjoins the first side to the second side; and the showerhead body containing a plurality of water ports on the second side for directing water flowing from the shower hose and a battery-powered vibrator to produce vibrations for external sexual stimulation, the plurality of water ports comprising a first water outlet zone on the second side on a first end near the shower hose and a second water outlet zone on an opposing end of the second side and separate from the first water outlet zone, and the battery-powered vibrator is positioned in the showerhead body between the first water outlet zone and the second water outlet zone.

2. The sexual stimulation device of claim 1, further comprising a regulator to control intensity of the vibrations from the vibrator.

3. The sexual stimulation device of claim 1, wherein the vibrator is removably engaged with the showerhead body.

4. The sexual stimulation device of claim 1, wherein the plurality of water ports is located on an anterior surface of the showerhead body.

5. The sexual stimulation device of claim 1, wherein the plurality of water ports is located on an anterior surface and a posterior surface of the showerhead body.

6. The sexual stimulation device of claim 2, wherein a plurality of controls for the regulator is located on a posterior surface of the showerhead body.

7. The sexual stimulation device of claim 2, wherein a button-operated control for the regulator is located between the shower hose-engaging structure and the showerhead body.

8. The sexual stimulation device of claim 1, wherein an exterior of the showerhead body is covered by a silicone sheath.

9. A sexual stimulation device, the device comprising:

a shower hose-engaging structure to connect a showerhead body to a shower hose, where the showerhead body has a first side and a second opposing side, each of the first side and the second side being substantially flat and curving toward an edge around the perimeter that adjoins the first side to the second side; and the showerhead body containing a plurality of water ports on the second side for directing water flowing from the shower hose and a water-powered vibrator to produce vibrations for external sexual stimulation, the plurality of water ports comprising a first water outlet zone on the second side on a first end near the shower hose and a second water outlet zone on an opposing end of the second side and separate from the first water outlet zone, and the battery-powered vibrator is positioned in the showerhead body between the first water outlet zone and the second water outlet zone.

10. The sexual stimulation device of claim 9, further comprising a regulator to control intensity of the vibrations from the vibrator.

11. The sexual stimulation device of claim 9, wherein the plurality of water ports is located on an anterior surface of the showerhead body.

12. The sexual stimulation device of claim 10, wherein a button-operated control for the regulator is located between the shower hose-engaging structure and the showerhead body.

13. The sexual stimulation device of claim 9, wherein an exterior of the showerhead body is covered by a silicone sheath.

14. The sexual stimulation device of claim 9, wherein an anterior surface of the showerhead body has a textured surface.

15. The sexual stimulation device of claim 9, wherein the showerhead body has a two-pronged structure with prongs extending parallel to each other from the showerhead body.

16. The sexual stimulation device of claim 14, wherein the plurality of water ports is located at the base of the two-pronged structure.

* * * * *